United States Patent
Marin et al.

(10) Patent No.: US 7,291,728 B2
(45) Date of Patent: Nov. 6, 2007

(54) SPIROLACTAMS AND THEIR SYNTHESIS

(75) Inventors: Pedro Noheda Marin, Madrid (ES); Manuel Bernabe Pajares, Madrid (ES); Sergio Maroto Quintana, Madrid (ES); Nuria Tabares Cantero, Madrid (ES)

(73) Assignee: Laboratories Del Dr. Esteve, S.A., Barcelona (ES)

( * ) Notice: Subject to any disclaimer, the term of this patent is extended or adjusted under 35 U.S.C. 154(b) by 315 days.

(21) Appl. No.: 10/846,466

(22) Filed: May 14, 2004

(65) Prior Publication Data

US 2005/0250759 A1   Nov. 10, 2005

(30) Foreign Application Priority Data

May 10, 2004  (EP) .................................. 04380104
May 10, 2004  (ES) .................................. 200401123

(51) Int. Cl.
  C07D 221/20    (2006.01)
  C07D 209/96    (2006.01)
  C07D 205/12    (2006.01)
  C07C 259/06    (2006.01)
  C07C 239/06    (2006.01)
(52) U.S. Cl. .................... 540/203; 548/408; 546/16; 564/170
(58) Field of Classification Search ............ None
  See application file for complete search history.

(56) References Cited

U.S. PATENT DOCUMENTS

| | | | |
|---|---|---|---|
| 4,680,388 A | | 7/1987 | Sundeen et al. |
| 5,648,484 A | * | 7/1997 | Wu .......................... 540/203 |
| 5,698,548 A | * | 12/1997 | Dugar et al. ........... 514/210.02 |
| 5,734,061 A | | 3/1998 | Ryckman |
| 2005/0250759 A1 | * | 11/2005 | Marin et al. ........... 514/210.05 |
| 2005/0261492 A1 | * | 11/2005 | Marin et al. ................ 540/203 |

FOREIGN PATENT DOCUMENTS

| WO | WO 94/17038 | 8/1994 |
|---|---|---|
| WO | WO 96/27587 | 9/1996 |

OTHER PUBLICATIONS

Greene and Wuts "Protective Groups in Organic Synthesis", John Wiley & Sons, Inc., New York, 1999 pp. 41, 113 and 114.*
Miyazawa et al., *Heterocycles*, vol. 59(1), pp. 149-160, Jan. 1, 2003.
Glover et al., *Tetrahedron*, vol. 43, pp. 2577-2592, 1987.
Kawase et al., *J. Org. Chem.*, vol. 54, pp. 3394-3403, 1989.
Kikugawa et al., *J. Org. Chem.*, vol. 68, pp. 6739-6744, Jul. 26, 2003.
Brown et al., *Tetrahedron*, vol. 51, pp. 11473-11488, 1995.
Mintz et al., *Org. Synthesis*, vol. 49, pp. 9-12, 1969.
Buu-Hoi et al., *Chimica Therapeutica*, pp. 39-48, 1967.
Cooley et al., *J. Org. Chem.*, vol. 40, pp. 552-557, 1975.
Dina-Telma et al., *Tetrahedron Letters*, vol. 35(13), pp. 2043-2046, 1994.
EPO, European Search Report for EP Application 04380104.2, Oct. 28, 2004.

* cited by examiner

Primary Examiner—Mark L. Berch
(74) Attorney, Agent, or Firm—Morgan & Finnegan, L.L.P.

(57) ABSTRACT

The present invention is directed to a compound of formula I:

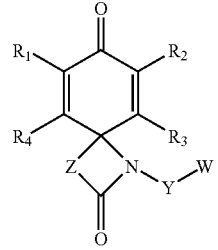

formula I wherein $R_1$ and $R_2$ are independently selected from H, halogen, protected or unprotected hydroxy, alkylsilyloxy, substituted or unsubstituted alkyl or cycloalkyl, substituted or unsubstituted alkoxy or aryloxy, substituted or unsubstituted aryl, substituted or unsubstituted heterocyclyl, nitro, amino, mercapto or alkylthio;

$R_3$ and $R_4$ are independently selected from H, substituted alkyl, substituted or unsubstituted alkoxy or aryloxy, substituted or unsubstituted aryl, substituted or unsubstituted heterocyclyl;

Z is —$(CR_aR_b)_n$— wherein n is a number selected from 1, 2, 3 and Ra and Rb are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy, substituted or unsubstituted amino or halogen;

Y is selected from —O—, —S—, —N(Ra)— or —C(O)—, wherein Ra is as previously defined and does not form a cyclic ring;

W is a group with sufficient electronic density to stabilize the compound through π interactions with the benzodienone moiety; or a salt thereof.

The present invention also provides a method for its synthesis and intermediates thereof, as well as a method for absorbing UV comprising exposing a compound of formula I to UV radiation.

25 Claims, No Drawings

SPIROLACTAMS AND THEIR SYNTHESIS

FIELD OF THE INVENTION

The present invention relates to new spirolactam compounds, to synthetic processes and intermediate compounds for their preparation and to their use as UV absorbers.

BACKGROUND OF THE INVENTION

Lactams are compounds of high interest due to their biological activities, for example well known β-lactams such as some penicillins, cephalosporins and carbapenems have antibacterial activity.

Spirolactams are one particular class of lactams that have shown interesting biological properties. Some spiro-fused azetidinones have been described as having antibacterial activity, see U.S. Pat. No. 4,680,388, or hypocholesterolemic properties, see for example WO 94 17038. Additionally, if these compounds have the adequate functionality they are valuable intermediates towards different families of compounds. The spirolactam ring is the equivalent of an alpha amino or hydroxy aminoacid and opens many possibilities in diastero and/or enantioselective synthesis.

There are few synthetic processes available for this class of compounds. WO 96 27587 describes the catalytic enantioselective synthesis of certain spirolactams that involves a large number of steps. U.S. Pat. No. 5,734,061 also describes a process for the preparation of spirocyclic lactams N-substituted with a tertiary amine susbtituent. U.S. Pat. No. 4,680,388 describes procedures to obtain N-sulphate substituted spirolactams. These processes and the intermediates used in them are directed to very particular compounds and therefore lack a wider applicability due to the absence of reactive functional groups.

Miyazawa, E. et al. in *Heterocycles*, vol 59, 1:149-160 "Synthesis of spiro-fused nitrogen heterocyclic compounds via N-methoxy-N-acylnitrenium ions using phenyliodine (III) bis(trifluoroacetate) in trifluoroethanol" describe another process to obtain functionalised spirolactams including some spirodienones.

Glover, S. A. et al. in *Tetrahedron*, 1987, 43:2577-2592 "N-alkoxy-N-acylnitrenium ions in intramolecular aromatic addition reactions" describe the synthesis in low yields of benzolactams via cyclization of N-alkoxy-N-acylnitrenium ions.

Kawase, M. et al. in *J. Org. Chem.*, 1989, 54:3394-3403 "Electrophilic aromatic substitution with N-methoxy-N-acylnitrenium ions generated from N-chloro-N-methoxyamides: syntheses of Nitrogen heterocyclic compounds bearing a N-methoxyamide group" describe among others the synthesis of spiro benzodienone lactams by ipso amidation with a nitrenium ion.

These processes present serious inconvenients relating to their yields and to the limited stability of the spiro-fused lactams obtained. Thus, any efficient process for producing functionalised spirolactam compounds in high yield, with various functionalities such as a benzodienone group, and if necessary with stereospecificity, would be a welcome contribution to the art.

SUMMARY OF THE INVENTION

The invention provides very stable spiro-fused azatidinones which are useful as intermediate compounds in the preparation of a variety of highly functionalised chemical structures, including, if necessary, diastero and/or enantioselective processes.

In one aspect the invention provides a compound of formula I:

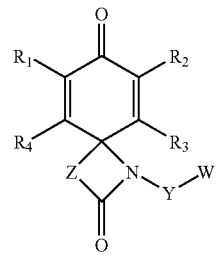

formula I wherein $R_1$ and $R_2$ are independently selected from H, halogen, protected or unprotected hydroxy, protected or unprotected silyloxy, substituted or unsubstituted alkyl or cycloalkyl, substituted or unsubstituted alkoxy or aryloxy, substituted or unsubstituted aryl, substituted or unsubstituted heterocyclyl, nitro, amino, mercapto or alkylthio;

$R_3$ and $R_4$ are independently selected from H, substituted alkyl, substituted or unsubstituted alkoxy or aryloxy, substituted or unsubstituted aryl, substituted or unsubstituted heterocyclyl;

Z is —$(CRaRb)_n$— wherein n is a number selected from 1, 2, 3 and Ra and Rb are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy, substituted or unsubstituted amino, or halogen;

Y is selected from —O—, —S—, —N(RaRb)— or —C(O)—, wherein Ra and Rb are as previously defined and do not form a cyclic ring;

W is a group with sufficient electronic density to stabilize the compound through π (pi) interactions with the benzodienone moiety;

or a salt, complex or solvate thereof.

We have drastically increased the stability of these compounds through the selection of an adequate W group.

As a further advantage, the compound adopts a preferential conformation in which the W group blocks one of the faces of the benzodienone, directing further reactions on the free face of the benzodienone moeity.

In addition, we have found that these compounds present interesting UV absorption properties which can be modulated according to the substituents used.

Preferably W is a group having unsaturated bonds or aromatic groups, more preferably it is selected from substituted or unsubstituted arylalkyl, substituted or unsubstituted heterocyclylalkyl, substituted or unsubstituted alkenyl.

The invention also provides a process for producing a compound of formula I which comprises a step (a) of reacting a compound of formula III:

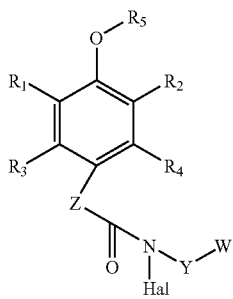

formula III wherein $R_1$, $R_2$, $R_3$, $R_4$, Z, Y, W are as defined above,
$R_5$ is hydrogen or substituted or unsubstituted alkyl;
Hal is F, Cl, Br, I or —SO$_2$CF$_3$;

with an N-acylnitrenium ion forming agent to produce a compound of formula I.

Preferably the process comprises the additional step (b) of preparing a compound of formula III by reacting a compound of formula IV:

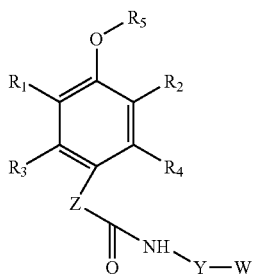

formula IV wherein wherein $R_1$, $R_2$, $R_3$, $R_4$, $R_5$, Z, Y, W are as defined above, with a Weinreb-type amide halogenating agent; preferably an agent selected from alkyl hypochlorite, alkyl hypobromite, sodium bromite, sodium hypochlorite, benzyltrimethylammonium trihalide, N-halophthalimide, N-halosuccinimide or phenyliodine (III) bis(trifluoroacetate) (PIFA). Most preferred is sodium hypochlorite.

Further, the invention provides intermediate compounds useful in the production of a compound of formula I as defined above, such as compounds III and IV.

DETAILED DESCRIPTION OF THE INVENTION

Previously described compounds such as N-methoxy substituted spiro-benzodienone are poorly stable and tend to reverse to compounds structurally related to the starting products during their synthesis or purification because of an easily triggered reduction process:

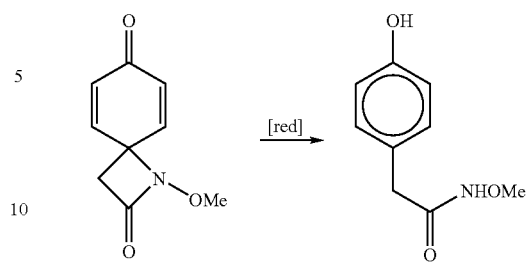

Additionally, during their synthesis or during their purification, and depending on the substitution of the phenyl acetamides starting materials, other aromatic heterocycles tend to be produced because of their higher stability (see *J. Org. Chem*, 1989, 54: 2294-3403, scheme I):

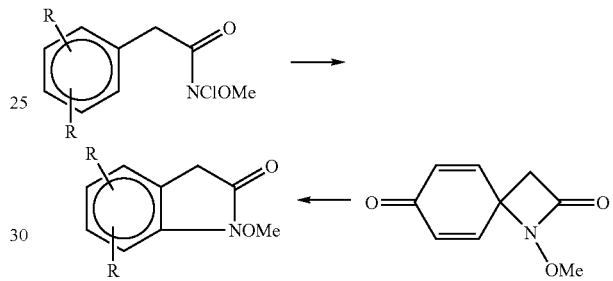

We have now found a new class of compounds containing the spirolactam group and presenting a benzodienone functionality that are remarkably stable and open to a large number of possibilities for further use. The stability is present during synthesis and also in purification processes. In these compounds the above mentioned reactions are avoided.

Without being bound by theory, we believe that the stability is provided by π interactions between the W group attached to the hydroxilamino and the benzodienone functionality. This configuration has a further advantage in that the W group covers one face of the benzodienone group, acting as a protecting group for one of the faces and directing the attack of further reactives to the other face.

In the above definition of compounds of formula (I) and in the description the following terms have the meaning indicated:

"Alkyl" refers to a straight or branched hydrocarbon chain radical consisting of carbon and hydrogen atoms, containing no saturation, having one to eight carbon atoms, and which is attached to the rest of the molecule by a single bond, e.g., methyl, ethyl, n-propyl, i-propyl, n-butyl, t-butyl, n-pentyl, etc. Alkyl radicals may be optionally substituted by one or more substituents independently selected from the group consisting of a halo, hydroxy, alkoxy, carboxy, cyano, carbonyl, acyl, alkoxycarbonyl, amino, nitro, mercapto and alkylthio.

"Alkoxy" refers to a radical of the formula -ORa where Ra is an alkyl radical as defined above, e.g., methoxy, ethoxy, propoxy, etc. "Aryloxy" refers to a radical of formula —ORb wherein Rb is an aryl radical as defined below.

"Amino" refers to a radical of the formula $-NH_2$, $-NHRa$, $-NRaRb$.

"Aryl" refers to a phenyl, naphthyl or anthracyl radical. The aryl radical may be optionally substituted by one or more substituents selected from the group consisting of hydroxy, mercapto, halo, alkyl, phenyl, alkoxy, haloalkyl, nitro, cyano, dialkylamino, aminoalkyl, acyl and alkoxycarbonyl, as defined herein.

"Aralkyl" refers to an aryl group linked to an alkyl group such as benzyl and phenethyl.

"Cycloalkyl" refers to a saturated carbocyclic ring having from 3 to 8 carbon atoms.

"Heterocycle" refers to a heterocyclyl radical. The heterocycle refers to a stable 3- to 15-membered ring which consists of carbon atoms and from one to five heteroatoms selected from the group consisting of nitrogen, oxygen, and sulfur, preferably a 4- to 8-membered ring with one or more heteroatoms, more preferably a 5- or 6-membered ring with one or more heteroatoms. For the purposes of this invention, the heterocycle may be a monocyclic, bicyclic or tricyclic ring system, which may include fused ring systems; and the nitrogen, carbon or sulfur atoms in the heterocyclyl radical may be optionally oxidised; the nitrogen atom may be optionally quaternized; and the heterocyclyl radical may be partially or fully saturated or aromatic. Examples of such heterocycles include, but are not limited to, azepines, benzimidazole, benzothiazole, furan, isothiazole, imidazole, indole, piperidine, piperazine, purine, quinoline, thiadiazole, tetrahydrofuran.

References herein to substituted groups in the compounds of the present invention refer to the specified moiety that may be substituted at one or more available positions by one or more suitable groups, e.g., halogen such as fluoro, chloro, bromo and iodo; cyano; hydroxyl; nitro; azido; alkanoyl such as a C1-6 alkanoyl group such as acyl and the like; carboxamido; alkyl groups including those groups having 1 to about 12 carbon atoms or from 1 to about 6 carbon atoms and more preferably 1-3 carbon atoms; alkenyl and alkynyl groups including groups having one or more unsaturated linkages and from 2 to about 12 carbon or from 2 to about 6 carbon atoms; alkoxy groups having one or more oxygen linkages and from 1 to about 12 carbon atoms or 1 to about 6 carbon atoms; aryloxy such as phenoxy; alkylthio groups including those moieties having one or more thioether linkages and from 1 to about 12 carbon atoms or from 1 to about 6 carbon atoms; alkylsulfinyl groups including those moieties having one or more sulfinyl linkages and from 1 to about 12 carbon atoms or from 1 to about 6 carbon atoms; alkylsulfonyl groups including those moieties having one or more sulfonyl linkages and from 1 to about 12 carbon atoms or from 1 to about 6 carbon atoms; aminoalkyl groups such as groups having one or more N atoms and from 1 to about 12 carbon atoms or from 1 to about 6 carbon atoms; carbocyclic aryl having 6 or more carbons, particularly phenyl or naphthyl and aralkyl such as benzyl. Unless otherwise indicated, an optionally substituted group may have a substituent at each substitutable position of the group, and each substitution is independent of the other.

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by a $^{13}C$- or $^{14}C$-enriched carbon or $^{15}N$-enriched nitrogen are within the scope of this invention.

Salts of compounds of the invention are synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent or in a mixture of the two. Generally, nonaqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, maleate, fumarate, citrate, oxalate, succinate, tartrate, malate, mandelate, methanesulphonate and p-toluenesulphonate.

The compounds of the invention may be in crystalline form either as free compounds or as solvates (e.g. hydrates) and it is intended that both forms are within the scope of the present invention. Methods of solvation are generally known within the art.

The compounds of the present invention represented by the above described formula (I) may include enantiomers depending on the presence of chiral centres or isomers depending on the presence of multiple bonds (e.g. Z, E). The single isomers, enantiomers or diastereoisomers and mixtures thereof fall within the scope of the present invention.

In the compound of formula I $R_3$ and $R_4$ are preferably H. Other substituents such as halogen or unsubstituted alkyl are more difficult to produce because of the formation of indol type of compounds instead of the lactam.

In the compound of formula I substituents $R_1$ and $R_2$ should not be strongly electrophilic because during the synthesis and depending on the method used they could difficult the attack of the nitrenium ion. Preferably they are each independently selected from hydrogen, halogen, susbtituted aryl, more preferably they are both hydrogen.

In the compounds of formula I, the group Z gives rise to a ring of 4, 5 or 6 members. Substitution on position Z creates a stereogenic center that could induce selective functionalisation on the benzodienone moiety. In a preferred embodiment Z is $—(CH_2)_n—$. Although rings of 5 or 6 are also comprised within the scope of the invention, in one embodiment the β-lactam ring (n=1) is preferred because of the further uses that can be given to such compounds.

The group Y in the compounds of formula I, plays a role in the stability and conformation and also during its synthesis. In an embodiment Y is preferably —O—, although other atoms are not excluded as long as the final product is stable.

As we already mentioned the W group is important for the stabilization of the compound of formula I. Preferably it comprises unsaturated bonds or aromatic groups to increase the pi interaction. Aralkyl groups and alkenyl groups are preferred since they give the best stability. In a particular embodiment, W is —CRaRb-Q or —SiRaRb-Q since the stability of the conformation is further improved by the presence of a —CRaRb- or a —SiRaRb-linker between Y and the substituent Q which has π (pi) interactions with the benzodienone moiety. The linker is preferably —CHRa—. In this case a stereogenic center is introduced which allows for the selectivity or specificity of any further reaction, distinguishing the two double bonds of the benzodienone. This will advantageously open the way to diastero- and/or enantioselective synthesis in addition to the selection for one face which is mentioned above. Depending on the size of Ra it can also modulate the π (pi) interactions and thus modulate properties such as UV absorption.

In one embodiment the W is an aralkyl group. Among the aryl groups susbtituted or unsubstituted phenyl and naphthyl are preferred. Heterocyclylalkyl groups are also envisaged.

In one embodiment the compounds of formula II are preferred:

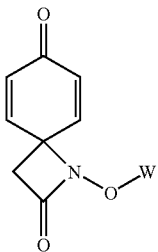

Formula II

Wherein W is as above defined. A particularly stable compound according to formula II has W=benzyl.

The compounds of formula (I) defined above can be obtained by available synthetic procedures. Some examples of these procedures are described in the documents mentioned above. Particularly good results are obtained forming the spiro lactam ring through reduction of an aromatic compound via a N-acylnitrenium ion.

Therefore in one aspect the invention is directed to a process of preparing a compound of formula I as defined above which comprises the step (a) of reacting a compound of formula III:

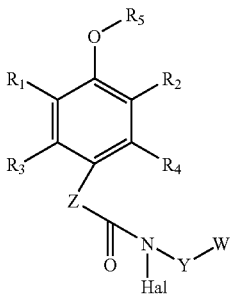

formula III wherein $R_1$, $R_2$, $R_3$, $R_4$, Z, Y, W are as defined above; $R_5$ is hydrogen or susbtituted or unsubstituted alkyl; Hal is F, Cl, Br, I or eventually —$SO_2CF_3$; with an N-acylnitrenium ion forming agent to produce a compound of formula I.

If Hal is an halogen, an adequate precipitating agent will be able to form the nitrenium ion. In general silver salts give good results, other salts can be used.

$R_5$ is preferably an electron-donating group, to promote the ipso addition of the nitrenium ion. Preferably $R_5$ is alkyl such as methyl, ethyl, propyl, etc. Most preferably it is methyl.

An adequately susbtituted amino group can be used as an alternative to the —$OR_5$ group, in this case the addition of the nitrenium ion will generate the iminium salt of the benzodienone which by hydrolysis generates the benzodienone. In this alternative, it is preferred that the substituents on the N atom be electro donating groups, such as dialkylamine. Another possibility is to use an halogen group instead of —$OR_5$ as described in *J. Org. Chem.*, 2003, 68: 6739-6744.

The reaction is preferably carried out in absence of light to avoid undesired radical reactions such the formation of the alkoxyamide starting material rather than ipso amidation (addition), or decomposition of compounds of formula III.

Preferably the solvent should be polar, such as for example trifluoroacetic acid or acetic acid. A temperature of about −10° C. to about 10° C. is preferred, more preferably of about 0° C. The reaction can be carried out under inert atmosphere if necessary. The obtained product of formula I can be purified following standard procedures such as evaporation, chromatography, phase separation (extraction). As previously mentioned the product is stable and can be stored for a prolonged period of time.

The compound of formula III is preferably prepared from a Weinreb-type amide compound of formula IV:

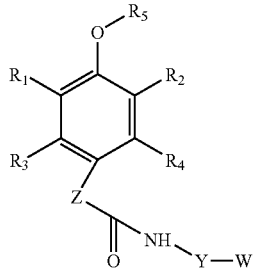

formula IV wherein $R_1$, $R_2$, $R_3$, $R_4$, $R_5$, Z, Y, W are as defined above, by reaction with an halogenating agent. The halogenating agent is preferably an agent selected from alkyl hypochlorite, alkyl hypobromite, sodium bromite, sodium hypochlorite, benzyltrimethylammonium trihalide, N-halosuccinimide, N-halophthalimide or phenyliodine (III) bis(trifluoroacetate) (PIFA). Sodium hypochlorite is preferred because of its low cost and availability.

The halogenation is preferably carried out in an apolar sovent, such as acetone, and at a temperature of about −10° C. to about 10° C., more preferably of about 0° C. The reaction is preferably carried out in absence of light to avoid undesired radical reactions.

The compounds of formula IV are either commercially available or easily prepared following known procedures as described for example in the above mentioned references.

The processes above described provide a quick and easy way (3 steps) to obtain the stable compounds of formula I.

The possibility of the preparation of new lactams, which are stable, densely functionalised and well suited to control further reactions opens a large number of possibilities for further use. The compounds of formula I are useful starting materials to produce a variety of chemical structures of interest. The double bond can be subjected to electrophilic attacks with for example hydroxylating agents, epoxydation agents, reduction agents, as well as cycloadditions and Michael reactions.

NMR and UV spectroscopic data (see examples section) for compounds described by formula I are in complete agreement with the presence of π interactions between their benzodienone portion and the Y-X substitution for the cases in which the π-electrons are adequately orientated.

Thus, from the comparison between the $^1$H NMR data (chemical shifts and coupling constants) for compounds 3a, 3b, 3c and 3d (examples of formula IV) and compounds 5a, 5b, 5c and 5d (examples of formula I) it became evident that compounds 5c and 5d have to present the above indicated π interactions. For compound 5d, the huge difference between the four signals assigned to the four protons of its benzodienone portion has to be correlated to the interaction between this moiety and its Y-X portion. In addition, we propose that this interaction is enhanced by a Thorpe-Ingold effect.

Furthermore, the UV data for compounds 3a, 3b, 3c and 3d (examples of formula IV) and compounds 5a, 5b, 5c and 5d (examples of formula I) (see examples section) support our conclusions from their $^1$H NMR data. While the spectra for 3a, 3b, 3c and 3d (examples of formula IV) present at 276 nm their maximum absorption ($\lambda_{max}$) and this is with independence of their Y-W substitution or Y-X, respectively, the situation for examples of formula I is completely different. Compounds 5a and 5b present at 243 nm their maximum absorptions ($\lambda_{max}$), and compounds 5c and 5b at 242 and 232 nm, respectively. The variation of 11 nm between the maximum absorption ($\lambda_{max}$) between compound 5d and compound 5a is assigned to the interaction between its benzodienone portion moiety and its Y-X portion.

The knowledge of the structural basis (the establishment of π interactions between their benzodienone portion and the Y-X substitution) for the above features spans the scope of their accessibility and applicability. From their absorption data it is clear that both the range of absorption and the possibility to modulate this range by selection of the appropriate substituents makes these compounds useful materials as UV absorbers.

The following examples are intended to exemplify the invention, and should not be construed as limiting the disclosure of the claimed invention.

EXAMPLES

General Methods and Materials.

All reactions described below were carried out under argon atmosphere unless otherwise noted. The solvents used were distilled and dried under argon atmosphere before use ($CH_2Cl_2$ and benzene were distilled over $CaH_2$). Flash Chromatography was executed on columns loaded with 230-400 mesh silica gel Merck. TLC was carried out on silica gel Merck (Kieselgel 60F-254).

All starting materials were purchased commercially (Aldrich, Fluka and Merck) and used without further purification, except the N-alcoxyamine 2d, which was prepared according to a literature procedure (see below). A commercial household bleach solution Mavy® which is stated to be <5% NaOCl was used for the preparation of t-butyl hypochlorite following the procedure described below.

Melting points (mp) were determined on a Reichert Microscopic Hot-Stage and are uncorrected. $^1$H and $^{13}$C NMR spectra were measured on a Varian Gemini-200 and a Varian Inova-300 spectrometer with $(CH_3)_4Si$ as an internal reference and $CDCl_3$ as solvent unless otherwise noted. Both $^1$H and $^{13}$C NMR spectral data are reported in parts per million (δ) relative to residual sign of the solvent ($CDCl_3$, 7.26 ppm and 77.0 ppm for $^1$H and $^{13}$C NMR, respectively). $^1$H and $^{13}$C NMR designations are: s (singlet); s br. (broad singlet); d (doublet); t (triplet); q (quartet); m (multiplet). Infrared (IR) spectra were recorded on a Perkin-Elmer FT-IR spectrometer. UV spectra were recorded on a Perkin-Elmer 402 spectrometer. Low-resolution mass (LRMS) spectra were obtained on a Hewlett Packard 5973 MSD spectrometer with a direct inlet system (EI) at 70 eV. Microanalytical data (E.A.) were obtained on a Perkin-Elmer 240C and Heraus CHN—O instruments at the Instrumental Analysis Department of Instituto de Química Orgánica General (C.S.I.C.).

Example 1

General Procedure for the Preparation of the N-Alcoxyamides 3a-d from the 4-Methoxyphenylacetyl Chloride (1)

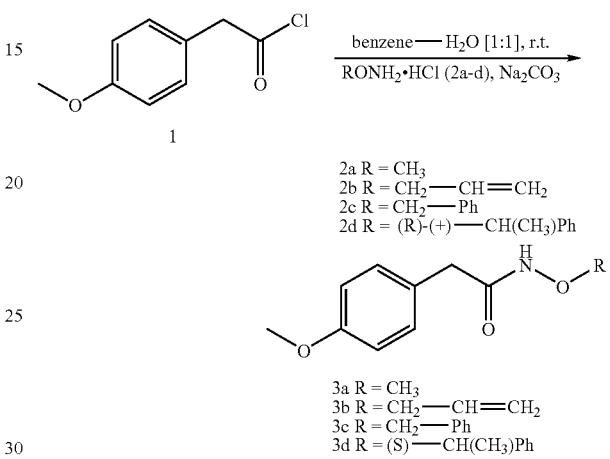

The N-alcoxyamines 2a-c were purchased from Aldrich and Fluka Companies, and used without further purification. The N-alcoxyamine 2d was prepared following the procedure described in Brown, D. S.; Gallagher, P. T.; Lightfoot, A. P.; Moody, C. J.; Slawin, A. M. Z.; Swann, E. *Tetrahedron* 1995, 51, 11473-11488.

To a vigorously stirred solution of N-alcoxyamine hydrochloride 2a-d (17.87 mmol) and sodium carbonate (32.50 mmol) in a mixture of benzene (23 ml) and $H_2O$ (23 ml) with ice-water bath cooling, was added 4-methoxyphenylacetyl chloride (1). The mixture was stirred at room temperature for 12 h under an argon atmosphere and the progress of the reaction was monitored by TLC (hexane-AcOEt, 1:2). Then, AcOEt (50 ml) was added and the organic layer separated. This process was repeated three times. The combined extracts were washed with brine (2×50 ml), dried over $Na_2SO_4$, filtered and concentrated under reduced pressure to give the corresponding N-alcoxyamide 3a-d, which was used in the next reaction without further purification.

Example 2

N-Methoxy-4-methoxyphenylacetamide (3a)

The compound was obtained from 1 and 2a as described in Kawase, M. et al *J. Org. Chem.*, 1989, 54:3394-3403 "Electrophilic aromatic substitution with N-methoxy-N-acylnitrenium ions generated from N-chloro-N-methoxyamides: syntheses of Nitrogen heterocyclic compounds bearing a N-methoxyamide group".

$R_f$=0.14 (TLC, hexane-AcOEt, 1:2); yield, 99%; white solid, mp 86-87° C. (lit. mp 83-85° C.); $^1$H-NMR (200 MHz, $CDCl_3$): δ 7.88 (1H, s br., NH), 7.19 (2H, d, J=8.7 Hz, H-2), 6.88 (2H, d, J=8.7 Hz, H-3), 3.81 (3H, s, $OCH_3$), 3.71 (3H, s, $NOCH_3$), 3.50 (2H, s, $CH_2$); $^{13}$C-NMR (75 MHz, $CDCl_3$):

δ 169.1, 158.5, 130.1, 126.1, 113.9, 63.8, 55.1, 39.1; IR (KBr): ν 3467, 3159, 2967, 1644, 1612, 1513, 1252, 1063, 1033 cm$^{-1}$; UV (MeOH): $\lambda_{max}$ (ε)=276 nm (1619 l.mol$^{-1}$.cm$^{-1}$); LRMS (EI): m/z 195 (M$^+$, 3), 165(1), 160(1), 148(6), 135(4), 121(100), 91(23), 78(66); E.A. ($C_{10}H_{13}NO_3$): calculated C, 61.53; H, 6.71. found C, 61.61; H, 6.76.

Example 3

N—(O-Allylhydroxyl)-4-methoxyphenylacetamide (3b)

Following the same procedure as in example 1 but starting from 2b we obtained compound 3b.

$R_f$=0.30 (TLC, hexane-AcOEt, 1:2); yield, 99%; white solid, mp 100-101° C.; $^1$H-NMR (200 MHz, CDCl$_3$): δ 7.85 (1H, s br., NH), 7.18 (2H, d, J=8.5 Hz, H-2), 6.87 (2H, d, J=8.5 Hz, H-3), 5.89 (1H, m, CH=CH$_2$), 5.31 (1H, s br., CH=CH$_2$), 5.25 (1H, s br., CH=CH$_2$), 4.32 (2H, d, OCH$_2$), 3.80 (3H, s, OCH$_3$), 3.49 (2H, s, CH$_2$); $^{13}$C-NMR (75 MHz, CDCl$_3$): δ 169.1, 158.5, 131.9, 130.0, 126.2, 120.2, 113.8, 76.9, 55.0, 39.2; IR (KBr): ν 3467, 2967, 1641, 1609, 1514, 1253, 1057 cm$^{-1}$; UV (MeOH): $\lambda_{max}$ (ε)=276 nm (2070 l.mol$^{-1}$.cm$^{-1}$); LRMS(EI): m/z 221(M$^+$, 37), 180(3), 161 (16), 148(33), 135(9), 121(100), 91(17), 78(31); E.A. ($C_{12}H_{15}NO_3$): calculated C, 65.14; H, 6.83. found C, 65.21; H, 6.89.

Example 4

N-Benzyloxy-4-methoxyphenylacetamide (3c)

Following the same procedure as in example 1 but starting from 2c we obtained compound 3c.

$R_f$=0.40 (TLC, hexane-AcOEt, 1:2); yield, 99%; white solid, mp 98-99° C.; $^1$H-NMR (200 MHz, CDCl$_3$): δ 7.71 (1H, s br., NH), 7.34 (5H, s br., Ph), 7.11 (2H, d, J=8.5 Hz, H-2), 6.83 (2H, d, J=8.5 Hz, H-3), 4.86 (2H, s, OCH$_2$Ph), 3.79 (3H, s, OCH$_3$), 3.45 (2H, s, CH$_2$); $^{13}$C-NMR (75 MHz, CDCl$_3$): δ 168.9, 158.5, 135.0, 130.0, 129.01, 128.4, 128.3, 126.0, 113.9, 77.8, 55.0, 39.3; IR (KBr): ν 3436, 3159, 2965, 1644, 1611, 1512, 1252, 1059, 1032, 726, 696 cm$^{-1}$; UV (MeOH): $\lambda_{max}$ (ε)=276 nm (1558 l.mol$^{-1}$.cm$^{-1}$); LRMS(EI): m/z 271(M$^+$, 14), 239(2), 211(6), 193(1), 180(2), 165(3), 148(5), 121(71), 91(100), 77(29); E.A. ($C_{16}H_{17}NO_3$): calculated C, 70.83; H, 6.32. found C, 70.87; H, 6.35.

Example 5

(−)-(S)-N-(1-Phenylethoxy)-4-methoxyphenylacetamide (3d)

Following the same procedure as in example 1 but starting from 2d we obtained compound 3d.

$R_f$=0.32 (TLC, hexane-AcOEt, 1:1); yield, 99%; white solid, mp 60-61° C.; $[\alpha]_D^{20}$=−168.2° (c 1.1, CHCl$_3$); $^1$H-NMR (200 MHz, CDCl$_3$): δ 7.56 (1H, s br., NH), 7.32 (5H, m, Ph), 6.98 (2H, d, J=7.1 Hz, H-2), 6.77 (2H, d, J=7.1 Hz, H-3), 4.98 (1H, m, OCH(CH$_3$)Ph), 3.78 (3H, s, OCH$_3$), 3.35 (2H, s, CH$_2$), 1.53 (3H, d, J=6.6 Hz, CH$_3$); $^{13}$C-NMR (75 MHz, CDCl$_3$): δ 168.5, 158.1, 140.6, 129.7, 128.0, 127.8, 126.6, 126.3, 113.5, 82.5, 54.7, 38.8, 20.4; IR (KBr): ν 3202, 3057, 2956, 2927, 2847, 1652, 1609, 1512, 1455, 1301, 1247, 1178, 1035, 700 cm$^{-1}$; UV (MeOH): $\lambda_{max}$ (ε)=276 nm (1841 l.mol$^{-1}$.cm$^{-1}$); LRMS(EI): m/z 285(M$^+$, 3), 268(2), 181(6), 165(2), 148(6), 121(40), 105(100), 91(5), 77(17); E.A. ($C_{17}H_{19}NO_3$): calculated C, 71.56; H, 6.71. found C, 71.62; H, 6.75.

Example 6

General Procedure for the Preparation of the Spiro-Lactams 5a-d

First, the compound t-Butyl Hypochlorite was prepared following the procedure described in Mintz, M. J.; Walling, C. *Org. Syntheses* 1969, 49, 9-12:

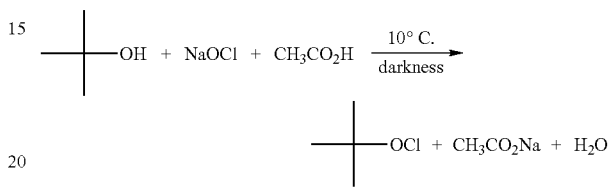

To a vigorously stirred commercial household bleach solution (500 ml) was added, at 10° C. in the dark and in a single portion, a solution of tert-butyl alcohol (37 ml, 0.39 mol) and glacial acetic acid (24.5 ml, 0.43 mol). The reaction mixture was stirred for about 3 min, and then was poured into separatory funnel. The lower aqueous layer was discarded, and the oily yellow organic layer was washed first with 10% aqueous Na$_2$CO$_3$ solution (50 ml) and then H$_2$O (50 ml). The product was dried over CaCl$_2$ (1 g) and filtered. The product can be stored in refrigerator over CaCl$_2$ in amber glass bottles. The t-butyl hypochlorite isolated by this procedure could be used in the next reaction without further purification.

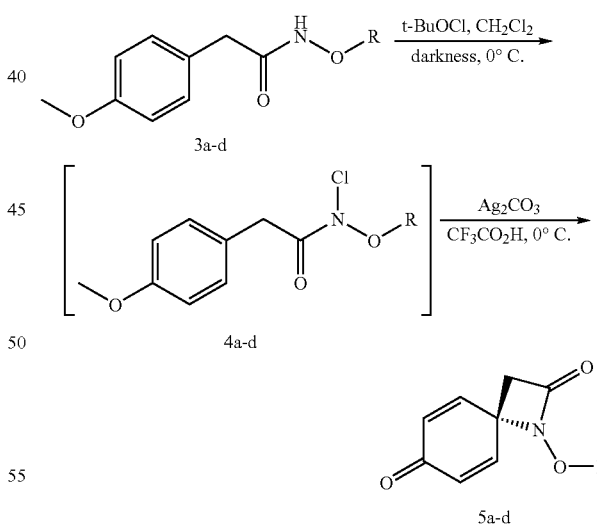

To a stirred solution of a N-alcoxyamide 3a-d (7.37 mmol) in CH$_2$Cl$_2$ (30 ml) was added slowly, at 0° C. in the dark, freshly prepared tert-butyl hypochlorite (9.21 mmol). Alternatively, sodium hypochlorite such as commercial household bleach solution Mavy® is used, at room temperature in the dark. The resulting mixture was stirred at 0° C. (or in the case of bleach added, at room temperature) in the dark under an argon atmosphere until the disappearance of starting material by TLC (hexane-AcOEt, 1:2) was observed (the time required was generally less than 30 min). The solvent was evaporated in the dark under reduced pressure and the residue, the N-chloro-N-alcoxyamide 4a-d as a yellow solid (Rf≈0.83, hexane-AcOEt, 1:2), was used in the next reaction without further purification.

To solid N-chloro-N-alcoxyamide 4a-d cooled at 0° C. and under an argon atmosphere, was added a solution of silver carbonate (14.74 mmol) in TFA (30 ml) in the dark with stirring. The mixture was stirred until the reaction was complete, generally 30 min (TLC monitoring, hexane-AcOEt, 1:2), and then the solvent was removed under pressure below 35° C. The residue was basified with 5% aqueous $Na_2CO_3$ solution (75 ml) with cooling. The precipitated silver salts were filtered through Celite in vacuum, and the pad was washed with $CH_2Cl_2$. The aqueous solution was extracted with $CH_2Cl_2$ (3×150 ml). The combined extracts was washed with brine (2×150 ml), dried over $Na_2SO_4$ and concentrated under reduced pressure. The residue was purified by silica gel column chromatography (hexane-AcOEt) to give the spiro β-lactam 5a-d.

1-Methoxy-1-azaspiro[3.5]nona-5,8-diene-2,7-dione (5a)

Flash chromatography (hexane-AcOEt, 1:1). $R_f$=0.33 (TLC, hexane-AcOEt, 1:2); yield, 43%; pale brown solid, mp 107-109° C.; $^1$H-NMR (200 MHz, $CDCl_3$): δ 6.91 (2H, d, J=10.2 Hz, CH═CHCO), 6.46 (2H, d, J=10.2 Hz, CH═CHCO), 3.77 (3H, s, $OCH_3$), 2.97 (2H, s, $CH_2$); $^{13}$C-NMR (75 MHz, $CDCl_3$): δ 184.2, 162.2, 145.5, 132.5, 65.5, 60.4, 43.6; IR (KBr): ν 3436, 3014, 2934, 1772, 1667, 1630, 1404, 1060, 880 $cm^{-1}$; UV (MeOH): $\lambda_{max}$ (ε)=243 nm (11959 $l.mol^{-1}.cm^{-1}$); LRMS(EI): m/z 179 (M$^+$, 1), 164(1), 151(2), 137(100), 106(3), 78(6); E.A. ($C_9H_9NO_3$): calculated C, 60.33; H, 5.06. found C, 60.39; H, 5.10.

1-(O-Allylhydroxyl)-1-azaspiro[3.5]nona-5,8-diene-2,7-dione (5b)

Flash chromatography (hexane-AcOEt, 3:2). $R_f$=0.40 (TLC, hexane-AcOEt, 1:2); yield, 68%; yellow oil; $^1$H-NMR (200 MHz, $CDCl_3$): δ 6.89 (2H, d, J=10.1 Hz, CH═CHCO), 6.44 (2H, d, J=10.1 Hz, CH═CHCO), 5.97-5.83 (1H, m, $CH_2$—CH═$CH_2$), 5.37 (1H, m, $CH_2$—CH═$CH_2$), 5.32 (1H, m, $CH_2$—CH═$CH_2$), 4.35 (2H, d, J=6.3 Hz, $CH_2$—CH═$CH_2$), 2.96 (2H, s, $CH_2$); $^{13}$C-NMR (75 MHz, $CDCl_3$): δ 183.9, 162.6, 145.7, 131.6, 131.4, 128.7, 77.8, 60.1, 42.9, 12.8; IR (NaCl, $CCl_4$): ν 3536, 3050, 2927, 1783, 1669, 1631, 1401, 1251, 1052, 940, 880, 839 $cm^{-1}$; UV (MeOH): $\lambda_{max}$ (ε)=243 nm (12549 $l.mol^{-1}.cm^{-1}$); LRMS (EI): m/z 205 (M$^+$, 1), 177(3), 163(79), 147(34), 133(36), 120(8), 106(89), 78(100); E.A. ($C_{11}H_{11}NO_3$): calculated C, 64.38; H, 5.40. found C, 64.44; H, 5.44.

1-Benzyloxy-1-azaspiro[3.5]nona-5,8-diene-2,7-dione (5c)

The purity of spiro-lactam 5c is related to the concentration of the household bleach solution used. $^1$H NMR spectra have to be used by the determination of spiro-lactam/N-alcoxyamide (5c:3c) ratio. By TLC both compounds have the same $R_f$ (0.40, hexane-AcOEt, 1:2). Flash chromatography (hexane-AcOEt, 2:1). $R_f$=0.40 (TLC, hexane-AcOEt, 1:2); yield, 68%; pale brown-reddish solid, mp 77-79° C.; $^1$H-NMR (200 MHz, $CDCl_3$): δ 7.32 (5H, m, Ph), 6.55 (2H, d, J=10.2 Hz, CH═CHCO), 6.17 (2H, d, J=10.2 Hz, CH═CHCO), 4.88 (2H, s, $OCH_2Ph$), 2.89 (2H, s, $CH_2$); $^{13}$C-NMR (75 MHz, $CDCl_3$): δ 183.8, 162.9, 145.0, 134.2, 130.9, 128.7, 128.6, 128.1, 78.7, 60.0, 42.9; IR (KBr): ν 3459, 3043, 2963, 1764, 1672, 1630, 1375, 1056, 886, 841, 768, 737, 696 $cm^{-1}$; UV (MeOH): $\lambda_{max}$ (ε)=242 nm (9511 $l.mol.cm^{-1}$); LRMS(EI): m/z 255(M$^+$, 1), 197(41), 121(6), 106(16), 91(100), 78(25); E.A. ($C_{15}H_{13}NO_3$): calculated C, 70.58; H, 5.13. found C, 70.63; H, 5.18.

(−)-(S)-1-(1-Phenylethoxy)-1-azaspiro[3.5]nona-5,8-diene-2,7-dione (5d)

Flash chromatography (hexane-AcOEt, 3:2). $R_f$=0.47 (TLC, hexane-AcOEt, 1:2); yield, 55%; brown oil; $[α]_D^{20}$=−63.6° (c 1.0, $CHCl_3$); $^1$H-NMR (200 MHz, $CDCl_3$): δ 7.30-7.17 (5H, m, Ph), 6.67 (1H, dd, J=10.0, 2.9 Hz, CH═CHCO), 6.23 (1H, dd, J=10.0, 2.0 Hz, CH═CHCO), 6.11 (1H, dd, J=10.0, 2,9 Hz, CH═CHCO), 5.81 (1H, dd, J=10.0, 2.0 Hz, CH═CHCO), 4.88 (1H, q, J=6.6 Hz, OCH($CH_3$)Ph), 2.75 (2H, s, $CH_2$), 1.44 (3H, d, J=6.6 Hz, $CH_3$); $^{13}$C-NMR (75 MHz, $CDCl_3$): δ 184.2, 163.8, 145.4, 144.9, 140.1, 131.9, 130.5, 128.9, 128.6, 127.1, 85.0, 60.5, 43.4, 20.7; IR (NaCl, $CCl_4$): ν 3289, 2978, 2927, 1784, 1668, 1630, 1512, 1454, 1249, 1050, 700 $cm^{-1}$; UV (MeOH): $\lambda_{max}$ (ε)=232 nm (3083 $l.mol^{-1}.cm^{-1}$); LRMS(EI): m/z 269(M$^+$, 1), 181(1), 165(1), 155(1), 148(1), 121(26), 105(100), 77(19); E.A. ($C_{16}H_{15}NO_3$): calculated C, 71.36; H, 5.61. found C, 71.40; H, 5.67.

The invention claimed is:

1. A compound of formula I:

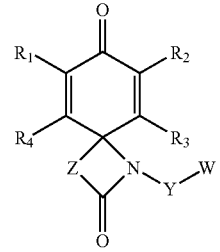

formula I wherein $R_1$ and $R_2$ are independently H, halogen, protected or unprotected hydroxy, trialkylsilyloxy, substituted or unsubstituted alkyl or cycloalkyl, substituted or unsubstituted alkoxy or aryloxy, substituted or unsubstituted aryl, substituted or unsubstituted heterocyclyl, nitro, amino, mercapto or alkylthio;

$R_3$ and $R_4$ are independently H, substituted alkyl, substituted or unsubstituted alkoxy or aryloxy, substituted or unsubstituted aryl, substituted or unsubstituted heterocyclyl;

Z is —(CRaRb)$_n$— wherein n is 1, and Ra and Rb are each independently hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy, substituted or unsubstituted amino or halogen;

Y is —O—, —S—, or —C(O);

W is —CRaRb-Q, wherein Ra and Rb are as previously defined and Q is substituted or unsubstituted aryl, substituted or unsubstituted heterocyclyl, substituted or unsubstituted alkenyl; or a salt thereof.

2. A compound as defined in claim 1 wherein $R_3$ and $R_4$ are H.

3. A compound as defined in claim 1 wherein $R_1$ and $R_2$ are each independently hydrogen, halogen or substituted aryl.

4. A compound as defined in claim 3 wherein $R_1$ and $R_2$ are H.

5. A compound as defined in claim 1 wherein Z is —(CHRa)$_n$—, Ra and n being as defined in claim 1.

6. A compound as defined in claim 5 wherein Ra is H.

7. A compound as defined in claim 1 wherein Y is —O—.

8. A compound as defined in claim 1 wherein Ra and Rb are H.

9. A compound as defined in claim 8 wherein Q is aryl.

10. A compound of formula II:

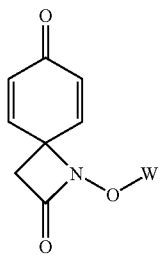

Formula II wherein W is as defined in claim 1.

11. A compound as defined in claim 10, wherein W is —CH$_2$-Q, and Q is substituted or unsubstituted aryl, substituted or unsubstituted alkenyl.

12. A compound as defined in claim 11, wherein Q is phenyl.

13. A process for producing a spirolactam compound as defined in claim 1 which comprises the step (a) of reacting a compound of formula III:

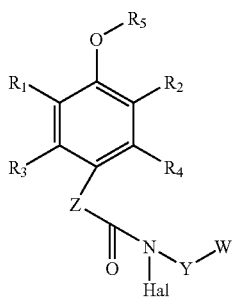

formula III wherein $R_1$, $R_2$, $R_3$, $R_4$, Z, Y, W are as defined in claim 1;
$R_5$ is hydrogen or substituted or unsubstituted alkyl;
Hal is F, Cl, Br, or I;
with an halogen precipitating agent to produce a compound of formula I.

14. A process as defined in claim 13 wherein the step (a) is carried out in the absence of light.

15. A process according to claim 13 which comprises the additional step (b) of preparing a compound of formula III by reacting a Weinreb-type amide compound of formula IV:

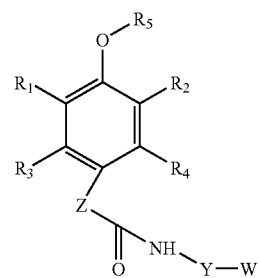

formula IV with a halogenating agent.

16. A process according to claim 15 wherein the halogenating agent is alkyl hypochlorite or sodium hypochlorite.

17. A process according to claim 15 which comprises the additional step (c) of producing the compound of formula IV by reacting a compound of formula V with a compound of formula VI:

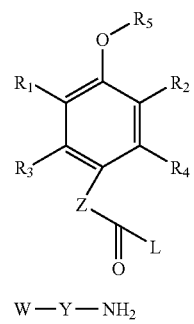

formula V

W—Y—NH$_2$   formula VI wherein W, Y, Z, R1, R2, R3, R4, R$_5$ are as previously defined and L is a nucleophilic leaving group.

18. A method of absorbing UV radiation comprising exposing a compound according to claim 1 to UV radiation.

19. The compound according to claim 1, wherein W is a substituted or unsubstituted arylalkyl, substituted or unsubstituted heterocyclylalkyl, substituted or unsubstituted alkenyl.

20. The compound according to claim 9, wherein Q is phenyl.

21. The compound according to claim 11, wherein Q is a substituted or unsubstituted phenyl or vinyl.

22. The process according to claim 13, wherein the halogen precipitating salt is a silver salt.

23. The process according to claim 15, wherein the halogenating agent is alkyl hypochlorite, alkyl hypobromite, sodium bromite, sodium hypochlorite, benzyltrimethylammonium trihalide, N-halosuccinimide, N-halophthalimide, or phenyliodine (III) bis(trifluoroacetate).

24. The process according to claim 16, wherein the alkyl hypochlorite is t-butyl hypochlorite.

25. The process according to claim 17, wherein the nucleophilic leaving group is a halogen.

* * * * *